United States Patent
Rigby et al.

(10) Patent No.: US 11,318,148 B2
(45) Date of Patent: *May 3, 2022

(54) PRESERVATIVE-FREE TREPROSTINIL DEVICES

(71) Applicant: SteadyMed, Ltd.

(72) Inventors: Jonathan Rigby, San Ramon, CA (US); Peter Noymer, Los Gatos, CA (US); Robert Zwolinski, Napa, CA (US)

(73) Assignee: SteadyMed, Ltd., Rehovot (IL)

( * ) Notice: Subject to any disclaimer, the term of this patent is extended or adjusted under 35 U.S.C. 154(b) by 208 days.

This patent is subject to a terminal disclaimer.

(21) Appl. No.: 16/828,145

(22) Filed: Mar. 24, 2020

(65) Prior Publication Data

US 2020/0237780 A1 Jul. 30, 2020

Related U.S. Application Data (62) Division of application No. 15/528,452, filed as application No. PCT/IL2015/051098 on Nov. 15, 2015, now Pat. No. 10,632,129.

(60) Provisional application No. 62/086,731, filed on Dec. 3, 2014.

(51) Int. Cl.
| | |
|---|---|
| *A61K 31/5575* | (2006.01) |
| *A61K 9/00* | (2006.01) |
| *A61M 5/142* | (2006.01) |
| *C07C 39/17* | (2006.01) |
| *C07C 59/72* | (2006.01) |
| *C07C 405/00* | (2006.01) |

(52) U.S. Cl.
CPC ........ *A61K 31/5575* (2013.01); *A61K 9/0019* (2013.01); *A61M 5/14248* (2013.01); *C07C 39/17* (2013.01); *C07C 59/72* (2013.01); *C07C 405/0075* (2013.01)

(58) Field of Classification Search
CPC ...... C07C 39/17; A61M 5/14248; A61K 9/19; A61K 31/5575
See application file for complete search history.

(56) References Cited

U.S. PATENT DOCUMENTS

2014/0296150 A1   10/2014  Hersel et al.

FOREIGN PATENT DOCUMENTS

| WO | 00/54758 A2 | 9/2000 |
| WO | 2013/140395 A1 | 9/2013 |

OTHER PUBLICATIONS

Database Biosis [Online] Biosciences Information Service, Philadelphia, PA, US; 2004, Kappelgaard Anne-Marie et al: "Liquid growth hormone: Preservatives and buffers", XP002753944, Database accession No. PREV200500077675 abstract & Hormone Research (Basel), vol. 62, No. Suppl. 3, 2004, pp. 98-103, ISSN: 0301-0163.
"Product monograph Remodulin", Sep. 25, 2008 (Sep. 25, 2008), XP055248060, Retrieved from the Internet: URL: http://shoppers-healthcare-portal-a88a1f4b.s3.amazonaws.com/AgilityUGC/88a5ba8f-045c-4147-86ef-8fe6f9bf5779/NE_PM00006673.pdf [retrieved on Feb. 5, 2016] p. 3: "Indications and clinical use" p. 7: table 1 p. 22: "Dosage forms, composition and packaging".
Rasmussen L H et al: "Authentic Recombinant Human Growth Hormone Results of a Multicenter Clinical Trial in Patients with Growth Hormone Deficiency", Helvetica Paediatrica ACTA, Schwabe, Basel, CH, vol. 43, No. 5-6, Jan. 1, 1988 (Jan. 1, 1988), pp. 443-448, XP009158145, ISSN: 0018-022X abstract p. 446, passage under heading "Results".
Highlights of Prescribing Information: Tyvasco—FDA report: 2002, pp. 1-16.
International Preliminary Report on Patentability for PCT/IL2015/051098 completed Mar. 24, 2017, all pages.
International Search Report and Written Opinion for PCT/IL2015/051098 dated Feb. 19, 2016, 10 pages.

*Primary Examiner* — Ana Z Muresan
(74) *Attorney, Agent, or Firm* — Kilpatrick Townsend & Stockton LLP (57) ABSTRACT

Embodiments include a system including a sealed prefilled drug-reservoir. The drug-reservoir may include a unit dosage of treprostinil in a sterile fluid composition. The composition may not include an antimicrobial preservative. The treprostinil may be present at a dosage of between 0.1 mg/mL and 25 mg/mL. In addition, the treprostinil may be treprostinil sodium Furthermore, the composition may include sodium chloride. The composition may also include a sodium ion from sodium chloride in a concentration from 3000 to 4500 ppm. The composition may not include metacresol.

16 Claims, 2 Drawing Sheets

PRESERVATIVE-FREE TREPROSTINIL DEVICES

CROSS-REFERENCES TO RELATED APPLICATIONS

This application is divisional of U.S. patent application Ser. No. 15/528,452, filed on May 19, 2017, which is a U.S. national phase under 35 U.S.C. § 371 of PCT International Application Number PCT/IL2015/051098, filed on Nov. 15, 2015, which claims the benefit of U.S. Provisional Patent Application No. 62/086,731, filed on Dec. 3, 2014. Each of these applications is hereby incorporated by reference in its entirety for all purposes.

BACKGROUND OF THE INVENTION

Pulmonary arterial hypertension (PAH) is an increase in blood pressure in the pulmonary artery, pulmonary vein, or pulmonary capillaries, leading to shortness of breath, dizziness, fainting, and other symptoms, all of which are exacerbated by exertion. PAH can be a severe disease with a markedly decreased exercise tolerance and heart failure. It is an orphan disease with an incidence of about 2-3 per million per year and a prevalence of about 15 per million. Median survival of patients with untreated PAH is in the range of 2-3 years from time of diagnosis, with the cause of death usually being right ventricular failure.

Pulmonary arterial hypertension involves the vasoconstriction or tightening of blood vessels connected to and within the lungs. Over time, fibrosis causes the affected blood vessels to become both stiffer and thicker which further increases the blood pressure within the lungs and impairs their blood flow. In addition, the increased workload of the heart causes hypertrophy of the right ventricle which ultimately causes right heart failure. As the blood flowing through the lungs decreases, the left side of the heart receives less blood and thus oxygen supply is below the required level, especially during physical activity.

A number of agents have been introduced for the treatment of PAH of which prostacyclins are commonly considered to be the most effective. One prostacyclin is Epoprostenol which is a synthetic prostacyclin and marketed as Flolan® (Glaxo SmithKline). It is given to patients via continuous infusion and requires a semi-permanent central venous catheter which can cause sepsis and thrombosis. Flolan® is unstable at room temperature, and therefore has to be kept on ice during administration. Since it has a half-life of only 3 to 5 minutes, the infusion has to be continuous night and day and any interruption can be fatal. Thus, treatment of PAH with Flolan® is a huge burden for the patient.

Therefore, there was a need to develop other prostanoids, as has been described for example in US4306075A and EP159784B1. One such prostaglandin is treprostinil with the trade name Remodulin® (United Therapeutics). The half-life of treprostinil is 4 hours but treprostinil is still required to be administered as a continuous subcutaneous infusion or continuous intravenous infusion via an infusion pump that the patient must wear at all times. Subcutaneous infusion of treprostinil is frequently painful to the extent that the patient cannot tolerate the pain and consequently the mode of administration is switched to intravenous infusion. However, an increased risk of sepsis with intravenous Remodulin has been reported. As subcutaneous infusion is associated with pain, there is a need for developing a prostacyclin that can be administered by subcutaneous administration but with reduced rates of pain.

Treprostinil was first described in U.S. Pat. No. 4,306,075. U.S. Pat. No. 5,153,222 discloses use of treprostinil for treatment of pulmonary hypertension. U.S. Pat. No. 5,234,953 discloses treatment of congestive heart failure with treprostinil. U.S. Pat. Nos. 6,765,117, 6,809,223, 8,524,939 and 8,658,837 disclose stereoselective process for treprostinil synthesis. U.S. Pat. Nos. 6,521,212 and 6,756,033 describe administration of treprostinil by inhalation for treatment of pulmonary hypertension, peripheral vascular disease and other diseases and conditions. U.S. Pat. No. 6,054,486 discloses treatment of peripheral vascular disease with Treprostinil. U.S. Pat. No. 6,803,386 discloses administration of treprostinil for treating cancer, such as lung, liver, brain, pancreatic, kidney, prostate, breast, colon and head-neck cancer. US patent application publication no. 2005/0165111 discloses treprostinil treatment of ischemic lesions. U.S. Pat. No. 7,199,157 discloses that treprostinil treatment improves kidney functions. US patent application publication no. 2005/0282903 discloses treprostinil treatment of diabetic neuropathic foot ulcers. US patent application publication no. 2008/0280986 discloses treatment of interstitial lung disease with Treprostinil. US patent application publication no. 2008/0200449 discloses administration of Treprostinil via a metered dose inhaler. US patent application publication no. 2009/0163738 discloses an alternative process for preparation treprostinil. U.S. Pat. Nos. 7,417,070; 7,384,978 and 7,544,713 disclose oral forms of treprostinil. US patent application publication no. 2009/0036465 discloses administration of treprostinil in combination with Rho-kinase inhibitors. U.S. provisional application No. 61/176,268 discloses solid formulations of treprostinil.

Treprostinil may be used in the treatment and/or prevention of/for: pulmonary hypertension, ischemic diseases (e.g. peripheral vascular disease including peripheral arterial disease, Raynaud's phenomenon including Raynaud's disease and Raynaud's syndrome, Scleroderma including systemic sclerosis, myocardial ischemia, ischemic stroke, renal insufficiency), ischemic ulcers including digital ulcers, heart failure (including congestive heart failure), conditions requiring anticoagulation (e.g., post MI, post cardiac surgery), thrombotic microangiopathy, extracorporeal circulation, central retinal vein occlusion, atherosclerosis, inflammatory diseases (e.g., COPD, psoriasis), hypertension (e.g., preeclampsia), reproduction and parturition, cancer or other conditions of unregulated cell growth, cell/tissue preservation and other emerging therapeutic areas where prostacyclin treatment appears to have a beneficial role.

Treprostinil may be administered via a small infusion pump that a patient must wear at all times. Treprostinil may be given subcutaneously using an infusion set, or intravenously via a central venous catheter if the patient is unable to tolerate the potential pain and discomfort of subcutaneous administration. Therefore, there exists a need to provide a more efficacious and/or more comfortable treprostinil treatment for patients.

BRIEF SUMMARY OF THE INVENTION

It is an object of this invention to provide a more efficacious and/or more comfortable treprostinil treatment for patients in need of same.

In some aspects of this invention, there is provided an aseptically filled, single-use container containing a parenteral formulation of treprostinil sodium without an antimicrobial preservative for subcutaneous or intravenous delivery to a subject in need of such treatment, which provides for reduced pain at an injection site. In some embodiments, methods for providing a reduced pain parenteral formulation of treprostinil sodium by treating a subject in need thereof with treprostinil sodium formulated without a preservative via subcutaneous or intravenous injection is envisioned, as well.

In some aspects, this invention provides a parenteral formulation of treprostinil sodium without an antimicrobial preservative for subcutaneous or intravenous delivery to a subject in need of such treatment, which formulation has a maximal volume of injection which does not exceed 10 mL. In some aspects, the formulation has a maximal value of injection which does not exceed from 8-10 mL, and in some embodiments, the formulation has a maximal value of injection which does not exceed from 5-10 mL, and in some embodiments, the formulation has a maximal value of injection which does not exceed from 5-8 mL, and in some embodiments, the formulation has a maximal value of injection which does not exceed from 2.5-5 mL, and in some embodiments, the formulation has a maximal value of injection which does not exceed from 1-5 mL, and in some embodiments, the formulation has a maximal value of injection which does not exceed from 1-2.5 mL, or in some embodiments, the formulation has a maximal value of injection which may be of any range of values from 1-10 mL.

In some aspects, this invention provides a method of reducing PAH pathogenesis in a patient treated with treprostinil, said method comprising treating a patient in need thereof with a parenteral formulation of treprostinil sodium without an antimicrobial preservative via subcutaneous or intravenous delivery to said subject, wherein removal of said antimicrobial preservative reduces the pathogenesis of PAH.

In some embodiments such method results in the ability to treat the patient with a reduced dosage or sustained dosage over a significantly prolonged period of time.

In some embodiments, such method results in less of a need to administer higher treprostinil dosages over time and in some embodiments, such method results in a less frequent need for adjustment of a dosages provided to such subject, over time, and in some embodiments, such method provides for a combination of these phenomena.

In some embodiments, such method results in an ability to administer a higher treprostinil dose in a given subject than was previously achievable, without negative effect. In some embodiments, such increased dosage is attainable, due to reduced infusion site pain, which in some aspects, limited tolerability and/or compliance with the administration of higher dosages in a given subject. In some embodiments, such increased dosage results in ultimate delivery of an optimal dose, which was not previously attainable in said subject. In some embodiments, such higher or optimal dosage may be obtained faster and in a smaller volume in a subject, than was attainable with comparable formulations containing a preservative.

In some aspects, the concentration of sodium chloride in the formulations of this invention are adjusted to offset the removal of the antimicrobial preservative in order to maintain isotonicity as desired for parenteral administration. In some aspects, the concentration of sodium chloride in the formulations of this invention are specifically adjusted to provide a hypotonic formulation for administration. In some aspects, the pH of the formulation is maintained at a value of from 6.5 to 6.7. In some aspects, the formulation is provided in multiple dose strengths in fine increments.

In some aspects, providing such formulation in fine concentration increments, enables a titratable delivery and without need of a user programmable pump, which is an advantage over existing similar delivery means. Without being bound by theory, in some embodiments, such formulation eliminates the potential for user and programming errors to cause adverse events for patients, which are typically encountered in pump-based devices. According to this aspect, and in some embodiments, existing pumps that are used for treprostinil administration are not designed specifically for the needs of PAH patients and introduce potential errors resulting in adverse effects. In some embodiments, the formulations, kits and methods of this invention obviate or reduce safety hazards such as overdoses, underdoses or missed doses.

This invention provides a unit dosage form of treprostinil sodium in a sterile fluid composition formulated for continuous subcutaneous or intravenous injection for periods up to 72 hours, wherein said composition does not comprise an antimicrobial preservative, and said treprostinil sodium is present at a dosage of between 0.1 mg/mL and 25 mg/mL.

In some embodiments, the composition does not comprise metacresol, other cresols and phenols, parabens, benzyl alcohol or any combinations thereof. In some embodiments, the composition does not comprise benzyl alcohol, chlorbutanol, 2-ethoxyethanol, methylparaben, propylparaben, butyl paraben, benzoic acid, sorbic acid, chlorhexidine, phenol, 3-cresol, thimerosal, phenylmercurate salts or the like.

In some embodiments, the sodium ion concentration ranges from 3300-4500 ppm, or any appropriate range to maintain isotonicity, or in some embodiments, the preparation of a slightly hypotonic formulation.

In some embodiments, the treprostinil sodium is formulated for delivery of a sub-clinical dosage, or in some embodiments, the subject is treated with a lower dosage for a sustained period of time, or in some embodiments, the dosage is titrated downward over time, which in some embodiments, is due to reduced pathogenesis of PAH than what is typically experienced with other Treprostinil treatment regimens in affected subjects.

This invention provides, in some aspects, a selectively activatable patch-pump assembly comprising a sealed pre-filled drug-reservoir containing the unit dosage form of treprostinil sodium in a sterile fluid composition formulated for subcutaneous injection as herein described.

In some embodiments, the invention provides a method of reducing pain at a site of subcutaneous or intravenous infusion of treprostinil in a subject in need thereof, wherein said subject is administered the unit dosage form of treprostinil sodium in a sterile fluid composition as herein described.

In some embodiments, the invention provides a method of reducing irritation, inflammation or a combination thereof at a site of subcutaneous or intravenous infusion of treprostinil in a subject in need thereof, wherein said subject is administered the unit dosage form of treprostinil sodium in a sterile fluid composition as herein described.

In some embodiments, the invention provides a method of treating pulmonary hypertension, comprising administering the unit dosage form of treprostinil sodium in a sterile fluid composition as herein described to a patient suffering from pulmonary hypertension.

In some embodiments, the invention provides a method for improving at least one kidney function in a subject with a disease or condition that causes kidney malfunction or failure, comprising administering to a subject in need thereof an effective amount of the unit dosage form of treprostinil sodium in a sterile fluid composition as herein described.

In some embodiments, the invention provides a method for treating a diabetic neuropathic foot ulcer, comprising administering to a subject with diabetic neuropathy in need thereof an effective amount of the unit dosage form of treprostinil sodium in a sterile fluid composition as herein described, wherein the subject has diabetic neuropathy.

In some embodiments, the invention provides a method for reducing or eliminating a pain associated with or caused by a diabetic neuropathic foot ulcer comprising administering to a subject with diabetic neuropathy in need thereof an effective amount of the unit dosage form of treprostinil sodium in a sterile fluid composition as herein described, wherein the subject has diabetic neuropathy.

In some embodiments, the invention provides a method for treating peripheral ischemic lesions on the skin of a subject, comprising administering to a subject in need thereof an effective amount of the unit dosage form of treprostinil sodium in a sterile fluid composition as herein described.

In some embodiments, the invention provides a method of treating critical limb ischemia comprising administering to a subject in need thereof an effective amount of the unit dosage form of treprostinil sodium in a sterile fluid composition as herein described.

DETAILED DESCRIPTION

This invention aims to provide a treprostinil treatment for patients in need of same, which is delivered over time via subcutaneous or intravenous administration, which treprostinil is formulated for subcutaneous or intravenous delivery in a sterile, single use fluid composition, providing, inter alia, for a minimal to no-pain setting for said subject, and in some embodiments, providing for reduced PAH pathogenesis than seen to date in subjects with PAH receiving alternate formulations of treprostinil.

In some aspects, the treprostinil sodium in provided as a sterile fluid composition formulated for subcutaneous or intravenous injection, wherein said composition does not comprise an antimicrobial preservative. In particular aspects, the composition does not comprise metacresol.

In some embodiments, the composition does not comprise metacresol, other cresols and phenols, parabens, benzyl alcohol or any combinations thereof. In some embodiments, the composition does not comprise benzyl alcohol, chlorbutanol, 2-ethoxyethanol, methylparaben, propylparaben, butyl paraben, benzoic acid, sorbic acid, chlorhexidine, phenol, 3-cresol, thimerosal, phenylmercurate salts or the like.

In some embodiments, the treprostinil sodium is formulated for delivery of a sub-clinical dosage, or in some embodiments, the subject is treated with a lower dosage for a sustained period of time than is typically administered in patients with PAH receiving treprostinil therapy, or in some embodiments, the dosage is titrated downward over time, which in some embodiments, is due to reduced pathogenesis of PAH than what is typically experienced with other Treprostinil treatment regimens in affected subjects.

In some embodiments, such method results in an ability to administer a higher treprostinil dose in a given subject than was previously achievable, without negative effect. In some embodiments, such increased dosage is attainable, due to reduced infusion site pain, which in some aspects, limited tolerability and/or compliance with the administration of higher dosages in a given subject. In some embodiments, such increased dosage results in ultimate delivery of an optimal dose, which was not previously attainable in said subject. In some embodiments, such higher or optimal dosage may be obtained faster and in a smaller volume in a subject, than was attainable with comparable formulations containing a preservative.

In some embodiments, the treprostinil sodium is provided in a single use container that provides therapy for one or several days at a time, and where such container can supply treprostinil at a rate of 0.1 to 50 mg per day. In some embodiments, the treprostinil sodium is provided in a single use container that provides therapy for one or several days at a time, and where such container can supply treprostinil at a rate of 0.1 to 25 mg per day, or in some embodiments, such container can supply treprostinil at a rate of 0.5 to 25 mg per day.

Surprisingly, removal of an antimicrobial preservative is associated not only with a reduction in pain at a site of injection, but also with reduced severe irritation/inflammation and/or severe pain at a site of injection. Referring to Example 3 and FIG. 2, in vivo studies in animals showed a demonstrable reduction in pain intensity at the infusion site when embodied treprostinil compositions were administered, as compared to essentially identical compositions, but for the presence of a preservative.

In some aspects, the same may be further associated with an improved responsiveness to treprostinil. In some aspects, such improved responsiveness may be seen in a sustained use of a relatively low dose, or in some embodiments, a slower time to increasing such dosage, or in some aspects, a titration downward of a dosage, or in some embodiments, a less frequent need for administration of treprostinil, or in some embodiments, any combination of these effects. In some aspects, the same may be further associated with improved tolerability of the therapy leading to an ability to increase the administered dosage to a higher dosage as needed, which was previously unattainable in the subject, or in some embodiments, the compositions/methods/kits of this invention provide for a reduced time to achieve higher tolerated doses in a subject than was heretofore attainable in the subject.

Treprostinil sodium is sometimes designated by the chemical names: (a) [(1R,2R,3aS,9aS)-2,3,3a,4,9,9a-hexahydro-2-hydroxy-1-[(3S)-3-hydroxyoctyl]-1H-benz [f]inden-5-yl]xy]acetic acid; or (b) 9-deoxy-2',9-a-methano-3-oxa-4,5,6-trinor-3,7-(1',3'-interphenylene)-13,14-dihydroprostaglandin Fl. Treprostinil sodium is also known as: UT-15; LRX-15; 15AU81; UNIPROSTTM; BW A15AU; and U-62,840. The molecular weight of Treprostinil sodium is 390.52, and its empirical formula is $C_{23}H_{34}O_5$. It should be understood that the invention encompasses any such form or known equivalent for same.

The Treprostinil as used in the compositions, devices and methods of the present invention are conveniently prepared by methods the same as or analogous to those described in U.S. Pat. Nos. 4,306,075, 6,528,688, 6,765,117, 6,441,245, 8,524,939 and U.S. Pat. No. 8,658,837.

The present invention extends to compositions, devices and methods of using physiologically acceptable salts of Treprostinil, as well as non-physiologically acceptable salts of Treprostinil that may be used in the preparation of the pharmacologically active compounds of the invention.

The term "pharmaceutically acceptable salt" refers to a salt of Treprostinil with an inorganic base, organic base, inorganic acid, organic acid, or basic or acidic amino acid. Salts of inorganic bases can be, for example, salts of alkali metals such as sodium or potassium; alkaline earth metals such as calcium and magnesium or aluminum; and ammonia. Salts of organic bases can be, for example, salts trimethylamine, triethylamine, pyridine, picoline, ethanolamine, diethanolamine, and triethanolamine. Salts of inorganic acids can be, for example, salts of hydrochloric acid, hydroboric acid, nitric acid, sulfuric acid, and phosphoric acid. Salts of organic acids can be, for example, salts of formic acid, acetic acid, trifluoroacetic acid, fumaric acid, oxalic acid, lactic acid, tartaric acid, maleic acid, citric acid, succinic acid, malic acid, methanesulfonic acid, benzenesulfonic acid, and p-toluenesulfonic acid. Salts of basic amino acids can be, for example, salts of arginine, lysine and ornithine. Salts of acidic amino acids can include, for example, salts of aspartic acid and glutamic acid. Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

Preferred pharmaceutically acceptable salts are disclosed, for example, in U.S. Pat. No. 8,497,393.

In some embodiments, reference to the compositions, kits and methods/uses of the invention, which refer to the term "comprise" or "comprising" also encompasses "consist of" or "consisting of."

In some embodiments, the unit dosage forms, compositions, kits and methods consist essentially of treprostinil, in a formulation, whereby the term "consist essentially of" specifically excludes the incorporation of an antimicrobial preservative.

In some embodiments, the unit dosage forms, compositions, kits and methods comprise or make use of treprostinil sodium. In some embodiments, the dosage forms, compositions, kits and methods consist or make use of treprostinil sodium. In some embodiments, the dosage forms, compositions, kits and methods consist essentially of or make use essentially of treprostinil sodium.

In some embodiments, the term "comprise" refers to the inclusion of the indicated active agent, such as the treprostinil, as well as inclusion of other active agents, and pharmaceutically acceptable carriers, excipients, emollients, stabilizers, etc., as are known in the pharmaceutical industry, however, such dosage forms/compositions/kits/methods of use, will not contain appreciable amounts of an antimicrobial preservative.

In some aspects, the reference to the compositions, kits, dosage forms, and methods which do not appreciable amounts of an antimicrobial preservative, refer to a less than 1.5%, or in some embodiments, less than 1%, or in some embodiments, less than 0.5%, or in some embodiments, less than 0.1%, or in some embodiments, less than 0.05%, or in some embodiments, less than 0.01%, or in some embodiments, less than 0.005%, or in some embodiments, less than 0.001%, of an antimicrobial preservative, and in some embodiments, the compositions, kits, dosage forms, and methods which do not appreciable amounts of an antimicrobial preservative, in fact do not contain any detectable amount of an antimicrobial preservative.

In some embodiments, the compositions of this invention will consist essentially of an active treprostinil ingredient. In some embodiments, the term "consisting essentially of" refers to a composition whose only active ingredient of a particular class of agents, is the indicated active ingredient, i.e. the only active prostacyclin is treprostinil, however, other compounds may be included which are involved directly in the therapeutic effect of the indicated active ingredient. In some embodiments, with reference to the compositions of this invention, when referring to a composition consisting essentially of an active treprostinil ingredient, such reference specifically excludes the incorporation of any antimicrobial preservative in the composition, in order to achieve a formulation which provides reduced or no pain at the site of injection of such composition and/or reduces irritation and/or inflammation at the site of injection.

"Pharmaceutical composition" or "composition" means a composition containing one or more drugs or prodrugs, and optionally one or more excipients, as well as any product which results, directly or indirectly, from combination, complexation or aggregation of any two or more of the excipients and/or the drug or prodrug, or from dissociation of one or more of the excipients and/or drug and/or prodrug, or from other types of reactions or interactions of one or more of the excipients and/or drug and/or prodrug. Accordingly, the pharmaceutical composition of the present invention encompasses any composition obtainable by admixing a carrier-linked treprostinil prodrug of the present invention and a pharmaceutically acceptable excipient.

The term "excipient" refers to a diluent, adjuvant, or vehicle with which the carrier-linked treprostinil prodrug is administered. Such pharmaceutical excipient can be sterile liquids, such as water and oils. In some aspects, saline and aqueous dextrose are preferred excipients when the pharmaceutical composition is administered intravenously.

Saline solutions and aqueous dextrose and glycerol solutions are preferably employed as liquid excipients for injectable solutions.

The composition, if desired, can also contain minor amounts of wetting or emulsifying agents, pH buffering agents, like, for example, acetate, succinate, tris, carbonate, phosphate, HEPES (4-(2- hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine.

Examples of suitable pharmaceutical excipients are described in "Remington's Pharmaceutical Sciences" by E. W. Martin. Such compositions will contain a therapeutically effective amount of treprostinil in the form of at least one carrier-linked treprostinil prodrug of the present invention, preferably in purified form, together with a suitable amount of excipient so as to provide the form for proper administration to the patient. The formulation should suit the mode of administration.

The term "pharmaceutically acceptable" means approved by a regulatory agency such as the EMA (Europe) and/or the FDA (US) and/or any other national or regional regulatory agency for use in animals, preferably in humans.

In some aspects, the amount of Treprostinil or its derivative, or a pharmaceutically acceptable salt thereof, which is provided in a medication or kit according to the invention is sufficient to achieve the desired effect, which in some aspects, will depend on the mode of administration (whether intravenous or subcutaneous), the concentration of the compound used, and the weight and condition of the patient.

For example, and providing guidance for the envisioned formulations and kits and applications in the methods of this invention, a daily dose may be in the range supplying treprostinil at a rate of 0.1 to 50 mg per day. In some embodiments, the treprostinil is provided in a daily dosage of 0.1 to 25 mg per day, or in some embodiments, daily dosage may supply treprostinil at a rate of 0.5 to 25 mg per day.

For example, a subcutaneous or intravenous dose may be provided in a unit dosage form supplying a daily dosage of 0.5 to 25 mg per day, which may conveniently be administered as an infusion, for example, using a pump compatible with the single-use container.

In some aspects, a subcutaneous or intravenous dose may be provided in a unit dosage form supplying a daily dosage of 0.5 to 25 mg per day, which dosage may still further be increased as needed, and as tolerated, and in some embodiments, the increase in dosage may be over a much prolonged period without ill effect, or in some embodiments, a lower dosage is necessary to achieve the desired therapeutic effect.

In some aspects, infusion fluids suitable for this purpose contain, for example, a delivery dosage of from 0.1 to 50 mg per day, provided in a minimal volume, which does not exceed 10 mL, as described hereinabove. In some embodiments, the treprostinil is formulated for delivery of a daily dosage of 0.1 to 25 mg per day, or in some embodiments, the treprostinil is formulated for delivery of a daily dosage of 0.5 to 25 mg per day in a minimal volume, which does not exceed 10 mL, as described hereinabove.

In the manufacture of a medicament or diagnostic aid according to the invention, hereinafter referred to as a "formulation," Treprostinil and/or its derivatives, and/or pharmaceutically acceptable salts thereof, may be admixed with, inter alia, an acceptable carrier. The carrier must, of course, be acceptable in the sense of being compatible with any other ingredients in the formulation and must not be deleterious to the subject. One or more of Treprostinil or its derivatives, or pharmaceutically acceptable salts thereof, may be incorporated in the formulations of the invention, which may be prepared by any of the well-known techniques of pharmacy for admixing the components.

It will be appreciated, however, that no preservatives will be included within the formulations and kits of this invention, nor used in accordance with the methods of this invention.

Formulations of the present invention suitable for parenteral administration conveniently comprise sterile aqueous preparations of Treprostinil or its derivative, or a pharmaceutically acceptable salt thereof, where the preparations may be isotonic or slightly hypotonic, with the blood of the intended recipient.

These preparations may be administered by means of subcutaneous injection, although administration may also be effected intravenously.

Such preparations may conveniently be prepared by admixing the compound with water or a glycine or citrate buffer and rendering the resulting solution sterile and isotonic with the blood.

Injectable formulations according to the invention may contain for example, a delivery dosage of from 0.1 to 50 mg per day, provided in a minimal volume, which does not exceed 10 mL, as described hereinabove. In some embodiments, the treprostinil is formulated as an injectable formulation for delivery of a daily dosage of 0.1 to 25 mg per day, or in some embodiments, the treprostinil is formulated as an injectable formulation for delivery of a daily dosage of 0.5 to 25 mg per day in a minimal volume, which does not exceed 10 mL, as described hereinabove.

In some embodiments, the sodium ion concentration ranges from 3000-4500 ppm, as appropriate in order to prepare isotonic or slightly hypotonic formulations as herein described.

In some aspects of the invention, the formulations of this invention comprise Treprostinil ranging in strength from 0.1 to 25 mg/mL in 0.5 mg/mL incrementsIn some embodiments, according to this aspect, the formulation will comprise a salt, such as sodium chloride at a range of from 4-6 mg/mL and in some embodiments, the formulation may further comprise trisodium citrate dihydrate, at a range of from about 5.5-7.0 mg/mL. In some embodiments, according to this aspect, the formulation will be adjusted for appropriate pH values and water is added as needed, depending on the batch size.

In some aspects of this invention, there is provided an aseptically filled, single-use container containing a parenteral formulation of treprostinil sodium without an antimicrobial preservative for subcutaneous or intravenous delivery to a subject in need of such treatment.

As will be appreciated by the skilled artisan, the terms "subject" and "patient" are used interchangeable and refer to any subject in need of or benefitting in any way from the described treatment/administration protocol/method of kit provided by the instant invention.

In some aspects, providing such formulation in fine concentration increments, enables a titratable delivery and without need of a user programmable pump, which is an advantage over existing similar delivery means by enabling titration and dose adjustments without the use of a programmable pump interface, as is required by current treatment modes. Programmable interfaces for this therapy, and for other therapies in general, can be problematic for patients in terms of being error prone, or requiring significant amounts of training and retraining, or both. There are not currently any infusion therapies with titration that do not have a requirement for programming the dose, and the formulation described herein enables the ability to achieve titration without programming.

This invention provides, in some aspects, a selectively activatable patch-pump assembly comprising a sealed prefilled drug-reservoir containing the unit dosage form of treprostinil sodium in a sterile fluid composition formulated for subcutaneous injection as herein described.

In some aspects, this invention provides an automatic injection device comprising a sealed prefilled drug-reservoir containing the unit dosage form of treprostinil sodium in a sterile fluid composition, which is preservative free, and formulated for subcutaneous injection as herein described.

In some embodiments, the term "automatic injection device" refers to a device that enables an individual (also referred to herein as a user or a patient or subject) to self-administer a dosage of a substance, such as a liquid medication, wherein the device differs from a standard syringe by the inclusion of a mechanism for automatically delivering the medication to the individual by injection when the mechanism is engaged.

In some aspects, as will be appreciated by the skilled artisan, any appropriate automatic injection device may be used, for example, as described in U.S. Pat. Nos. 3,910,260; 4,004,577; 4,689,042; 4,755,169; 4,795,433; 3,941,130; 4,261,358; 5,085,642; 5,092,843; 5,102,393;

5,267,963; 6,149,626; 6,270,479; 8,679,061 and 6,371,939, each of which is incorporated by reference herein in its entirety.

In some aspects, as will be appreciated by the skilled artisan, the unit dosage form of treprostinil in a sterile fluid composition is formulated for incorporation within a patch pump device as described or broadly contemplated in U.S. Pat. No. 9,011,376, or U.S. patent application Ser. No. 13/956,965, U.S. Pat. No. 8,834,454, U.S. patent application Ser. No. 13/825,806 or U.S. patent application Ser. No. 14/384,152, all of which are hereby incorporated by reference in their entirety.

In some aspects, the unit dosage form of treprostinil in a sterile fluid composition formulated for incorporation within a patch pump device as described, is specifically included in a reservoir comprised of Cyclic Olefin Polymer (COP), as opposed to polyvinyl chloride (PVC), polypropylene (PP) or glass. In some aspects, despite the use of the unconventional material for the reservoir, nonetheless, the formulation remains stable, and/or has the described advantages noted herein.

In some aspects, this invention provides a kit comprising a parenteral formulation of treprostinil sodium without an antimicrobial preservative for subcutaneous or intravenous delivery to a subject in need of such treatment, which provides for reduced pain at an injection site. In some aspects, such kits may provide multiple sterile parenteral formulations of treprostinil sodium without an antimicrobial preservative for subcutaneous or intravenous delivery, which vary in terms of the dosage delivered of same.

In some aspects, such kits comprise a container, which may include a vial, for injection, or in some embodiments, one or more prefilled drug-reservoirs containing the treprostinil formulation comprising treprostinil in a pharmaceutically acceptable carrier. In some aspects, the kits may further comprise instructions, such as a product insert or label, directing the user regarding proper administration and use of the formulation, or in some embodiments, instructions for making use of the formulations varying, for example in terms of tresprostinil dosage provided with said kit, which in some embodiments, provides instructions for titrating a dosage of same.

In some aspects, such kits may comprise a tubing set to connect the drug reservoir to the patient's cannula or catheter (also referred to herein as the means of administration), or in some embodiments, the means of administration is provided to the patient integrated with the container.

In some embodiments, the invention provides a method of reducing pain at a site of subcutaneous or intravenous infusion of treprostinil in a subject in need thereof, wherein said subject is administered the unit dosage form of treprostinil sodium in a sterile fluid composition as herein described or in some embodiments, the subject is administered treprostinil by making use of a kit as herein described.

In some embodiments, the invention provides for a composition for subcutaneous or intravenous infusion of treprostinil in a subject in need thereof, wherein said subject is administered the unit dosage form of treprostinil sodium in a sterile fluid composition as herein described or in some embodiments, the subject is administered treprostinil by making use of a kit as herein described.

In some embodiments, the invention provides a method of reducing irritation, inflammation or a combination thereof at a site of subcutaneous or intravenous infusion of treprostinil in a subject in need thereof, wherein said subject is administered the unit dosage form of treprostinil sodium in a sterile fluid composition as herein described or in some embodiments, the subject is administered treprostinil by making use of a kit as herein described.

In some embodiments, the invention provides a composition for reducing irritation, inflammation or a combination thereof at a site of subcutaneous or intravenous infusion of treprostinil in a subject in need thereof, wherein said subject is administered the unit dosage form of treprostinil sodium in a sterile fluid composition as herein described or in some embodiments, the subject is administered treprostinil by making use of a kit as herein described.

In some embodiments, the invention provides a method of treating pulmonary hypertension, comprising administering the unit dosage form of treprostinil sodium in a sterile fluid composition as herein described to a patient suffering from pulmonary hypertension or in some embodiments, the subject is administered treprostinil by making use of a kit as herein described.

In some embodiments, the invention provides a composition for treating pulmonary hypertension, wherein said subject is administered the unit dosage form of treprostinil sodium in a sterile fluid composition as herein described or in some embodiments, the subject is administered treprostinil by making use of a kit as herein described.

In some embodiments, the invention provides a method for improving at least one kidney function in a subject with a disease or condition that causes kidney malfunction or failure, comprising administering to a subject in need thereof an effective amount of the unit dosage form of treprostinil sodium in a sterile fluid composition as herein described or in some embodiments, the subject is administered treprostinil by making use of a kit as herein described.

In some embodiments, the invention provides a composition for improving at least one kidney function in a subject with a disease or condition that causes kidney malfunction or failure, wherein said subject is administered the unit dosage form of treprostinil sodium in a sterile fluid composition as herein described or in some embodiments, the subject is administered treprostinil by making use of a kit as herein described.

In some embodiments, the invention provides a method for treating a diabetic neuropathic foot ulcer, comprising administering to a subject with diabetic neuropathy in need thereof an effective amount of the unit dosage form of treprostinil sodium in a sterile fluid composition as herein described, or in some embodiments, the subject is administered treprostinil by making use of a kit as herein described wherein the subject has diabetic neuropathy.

In some embodiments, the invention provides a composition for treating a diabetic neuropathic foot ulcer, wherein said subject is administered the unit dosage form of treprostinil sodium in a sterile fluid composition as herein described or in some embodiments, the subject is administered treprostinil by making use of a kit as herein described.

In some embodiments, the invention provides a method for reducing or eliminating a pain associated with or caused by a diabetic neuropathic foot ulcer comprising administering to a subject with diabetic neuropathy in need thereof an effective amount of the unit dosage form of treprostinil sodium in a sterile fluid composition as herein described, or in some embodiments, the subject is administered treprostinil by making use of a kit as herein described wherein the subject has diabetic neuropathy.

In some embodiments, the invention provides a composition for reducing or eliminating a pain associated with or caused by a diabetic neuropathic foot ulcer, wherein said subject is administered the unit dosage form of treprostinil sodium in a sterile fluid composition as herein described or in some embodiments, the subject is administered treprostinil by making use of a kit as herein described.

In some embodiments, the invention provides a method for treating peripheral ischemic lesions on the skin of a subject, comprising administering to a subject in need thereof an effective amount of the unit dosage form of treprostinil sodium in a sterile fluid composition as herein described or in some embodiments, the subject is administered treprostinil by making use of a kit as herein described.

In some embodiments, the invention provides a composition for treating peripheral ischemic lesions on the skin of a subject, wherein said subject is administered the unit dosage form of treprostinil sodium in a sterile fluid composition as herein described or in some embodiments, the subject is administered treprostinil by making use of a kit as herein described.

In some embodiments, the invention provides a method of treating critical limb ischemia comprising administering to a subject in need thereof an effective amount of the unit dosage form of treprostinil sodium in a sterile fluid composition as herein described or in some embodiments, the subject is administered treprostinil by making use of a kit as herein described.

In some embodiments, the invention provides a method for treating, or reducing the severity or reducing the pathogenesis of Pulmonary arterial hypertension (PAH) in a subject, comprising administering to a subject in need thereof an effective amount of treprostinil in a sterile fluid composition, wherein said composition is formulated for subcutaneous or intravenous injection, said composition does not comprise an antimicrobial preservative, and said treprostinil is present at a dosage of between 0.1 mg/mL and 25 mg/mL.

In some embodiments, the invention provides a composition for treating, or reducing the severity or reducing the pathogenesis of Pulmonary arterial hypertension (PAH) in a subject, wherein said subject is administered the unit dosage form of treprostinil sodium in a sterile fluid composition as herein described or in some embodiments, the subject is administered treprostinil by making use of a kit as herein described.

According to this aspect, and in one embodiment, the subject has been previously treated with treprostinil in a formulation containing a preservative. According to this aspect, and in one embodiment, the preservative is metacresol. According to this aspect, and in one embodiment, the treprostinil is in a composition which does not contain an antimicrobial preservative reduces the pathogenesis of PAH. According to this aspect, and in one embodiment, the method provides for reducing a dosage of treprostinil over time. According to this aspect, and in one embodiment, the method provides for sustaining a given dosage over a prolonged period of time. According to this aspect, and in one embodiment, the method provides for reducing the necessity or reducing the intervals in which administration of an increased dosage of treprostinil is necessary, or a combination thereof.

In some embodiments, the invention provides a method for optimally treating, or reducing the severity or reducing the pathogenesis of Pulmonary arterial hypertension (PAH) in a subject, comprising administering to a subject in need thereof an effective amount of treprostinil in a sterile fluid composition, wherein said composition is formulated for subcutaneous or intravenous injection, said composition does not comprise an antimicrobial preservative, and said treprostinil is present at a dosage of between 0.1 mg/mL and 50 mg/mL.

According to this aspect, and in one embodiment, the subject has been previously treated with treprostinil in a formulation containing a preservative. According to this aspect, and in one embodiment, the preservative is metacresol. According to this aspect, and in one embodiment, the method provides for administering treprostinil at a higher dosage than previously tolerated in said subject in previous treatment of said subject. According to this aspect, and in one embodiment, the method provides for increasing a dosage of treprostinil over time. According to this aspect, and in one embodiment, the method provides for sustaining an increased dosage over a prolonged period of time. According to this aspect, and in one embodiment, the method provides for reducing the necessity or reducing the intervals in which administration of a further increased dosage of treprostinil is necessary, or a combination thereof.

It is to be understood that the advantages that have been described for use of the formulations in the treatment of PAH are, in some embodiments, effective advantages for application in any method as herein described.

All publications and patents mentioned herein are hereby incorporated by reference in their entirety as if each individual publication or patent was specifically and individually indicated to be incorporated by reference. In case of conflict, the present application, including any definitions herein, will control.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXAMPLES

Treprostinil Containing Formulations for Subcutaneous Delivery

Example 1

Figure 1A:
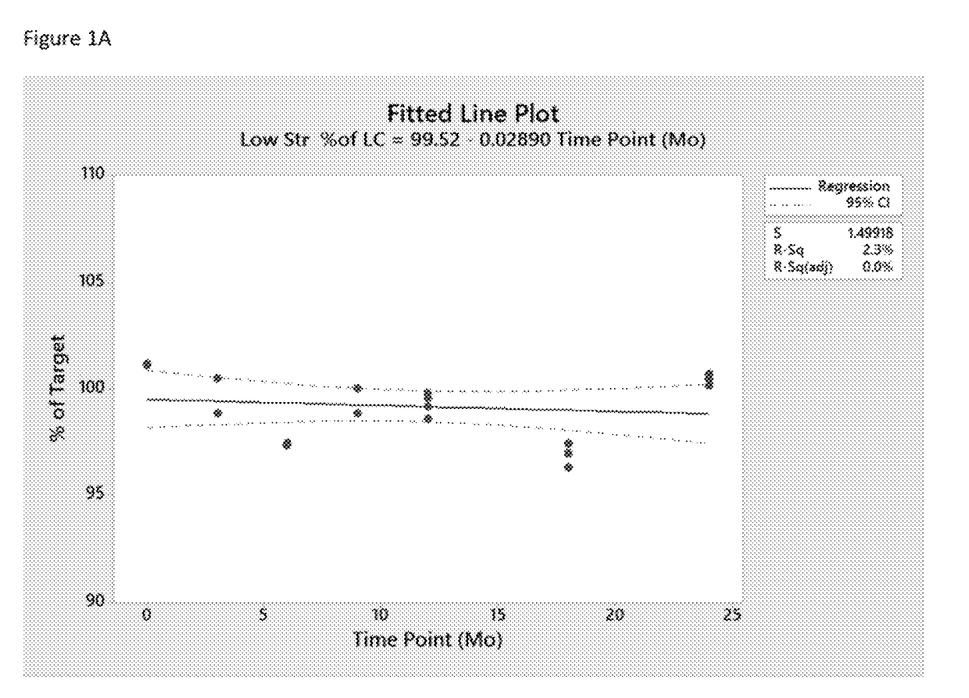
FIG. 1A and FIG. 1B plot formulation stability of two compositions according to embodiments of the present invention.
Figure 1B:
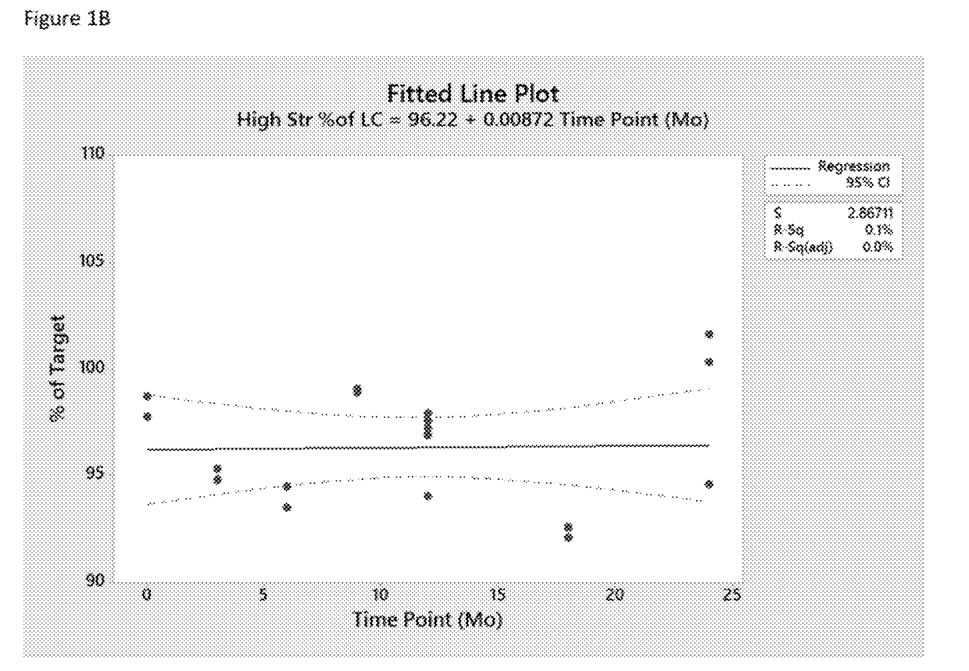

Embodied compositions have been prepared containing the following:
Treprostinil (formulation strength): 0.5 to 10 mg/mL in various increments
Sodium Chloride, USP: 5.3 mg/mL
Trisodium citrate dihydrate, USP: 6.3 mg/mL
1N HCl or IN NaOH, USP: As needed for pH adjustment
Water for injections: As needed per batch size The formulation is sterile filtered, aseptically filled into pre-sterilized unit dose containers, and stoppered, prior to assembly within an integrated delivery system. The formulations prepared have been shown to be stable for up to a minimum of 18 months. FIGS. 1A-1B plot formulation stability of two embodied compositions of this invention. Note that the x-axis represents time (in months) since the start of the study and the y-axis plots the % potency of the composition over time. The trendlines are essentially flat showing good stability in the single-use container. FIG. 1B plots the results for a formulation with a concentration of 0.5 mg/mL treprostinil, and FIG. 1A plots the results for a formulation with a concentration of 6.0 mg/mL treprostinil. The y-axis is normalized so that 100% represents either 0.5 or 6.0, respectively.

Reduction of Local Injection Site Effects Following Parenteral Administration of an Embodied Formulation Example 2

In order to compare the behavioral response and local tolerability of formulations with and without m-cresol, an in vivo rat model is pursued. Male rats are administered treprostinil via continuous subcutaneous infusion with, for example, an iPrecio pump, for an up to one week duration. Various groups may be assessed, including a first group receiving a formulation for subcutaneous injection of treprostinil with meta-cresol in a saline carrier or alternate excipient, a second group receiving the same formulation without metacresol, a third group receiving the same formulation without treprostinil and a fourth group receiving the same formulation without treprostinil or metacresol.

As study endpoints, analysis of the formulation dosage is verified and mortality assessed. In some aspects, cage side clinical observations are performed daily. Body weights may be assessed over time, for example, at pretreatment, Day 4 post-treatment and prior to termination.

In some aspects, behavioral endpoints will be recorded. Mechanical hyperalgesia may be assessed at various times, for example, at pretreatment, and on days 1, 4, and 7 post treatment. In another aspect, measurement of the response to Von Frey hairs applied at or around the infusion site will be assessed as well.

In another aspect, a modified Irwin battery is conducted [Irwin S (1968) Comprehensive observational assessment: IA. A systematic, quantitative procedure for assessing the behavioral and physiologic state of the mouse. Psychopharmacologia 13:222-257], assessed at pretreatment, and on days 1, 4, and 7 post treatment, with same preceding mechanical hyperalgesia measurements.

In another aspect, locomotor activity is assessed, for example at pretreatment, and days 2 and 6 post treatment.

In one aspect, automated instrumentation is employed, which measures photobeam breaks and assesses general behavior of the subjects, including activity and exploratory and rearing behavior.

In some aspects, necropsy is performed at the experimental end date, for example, on day 8. Animals are euthanized and gross observations of infusion site histopathology and other aspects are recorded. The infusion site and surrounding area will be evaluated microscopically by a board certified veterinary pathologist. Evaluation is conducted and severity scores ranging from 1 to 4 are assigned for each observation.

Reduction of Local Injection Site Effects Following Parenteral Administration of an Embodied Formulation Example 3

Similar in principle to studies described in Example 2, different formulations were prepared as described below and the effect of the formulation compositions on tactile sensitivity in rats was assessed in vivo.

Materials and Methods

The animal study design consisted of six dosing arms with n=10 rats per arm. In each arm, animals were dosed for 7 days via continuous subcutaneous (SC) infusion and tactile sensitivity assessments were made on Day 1 (baseline), Day 3 and Day 7.

The formulations used in the six arms were as follows: (1) saline, (2) vehicle without m-cresol, (3) vehicle with m-cresol, (4) treprostinil without m-cresol, (5) treprostinil with m-cresol, and (6) capsaicin, with arms 1 and 6 serving as negative and positive controls, respectively. The m-cresol concentration in arms 3 and 5 was 12 mg/mL to achieve the same mg/hour flow rate as would be found in human dosing. The treprostinil concentration in arms 4 and 5 was 0.054 mg/mL to achieve a dose level of roughly 30 ng/kg/min in the rats.

Tactile sensitivity measurements were made using an electronic Von Frey probe, in which the grams of force required to induce a physical response when the probe was pressed at the infusion site was recorded. Accordingly, the lower the measurement (fewer grams of force required to induce a response), the more tactile sensitivity there is.

Results

An electronic Von Frey probe was utilized to probe the effect of the two treprostinil arms (i.e. with and without the preservative m-cresol) on tactile sensitivity and the results, as compared to baseline (i.e. changes with respect to values obtained on Day 1 and after subtracting effects of administration of saline alone) showed treprostinil treatment, when formulated with m-cresol resulted in substantially greater sensitivity in the animals as evidenced by results obtained on Days 3 and 7, as compared to treprostinil treatment in a formulation without m-cresol.

It is known that when assessing force applied when the Von Frey probe is pressed at the infusion site, as the force decreases, the tactile sensitivity increases, i.e. any reduction in force applied signified higher degrees of pain to the animal.

Tables 1-3 below show the measured applied force as a function of time in a given animal. Table 1 shows the values obtained when saline was infused, versus treprostinil without and with m-cresol, respectively (Tables 2 and 3).

TABLE 1

SALINE
Table 1

| Rat # | Day 1 | Day 3 | Day 7 |
|---|---|---|---|
| B1 | 33.0 | 56.5 | 46.1 |
| B2 | 51.1 | 43.8 | 40.1 |
| B3 | 31.4 | 39.0 | 35.4 |
| B4 | 36.2 | 48.4 | 34.6 |
| B5 | 30.9 | 23.1 | 36.3 |
| B6 | 36.9 | 35.3 | 38.7 |
| B7 | 32.7 | 38.3 | 33.3 |
| B8 | 30.5 | 36.1 | 37.6 |
| B9 | 39.8 | 27.1 | 28.8 |
| B10 | 37.5 | 28.2 | 42.3 |

TABLE 2

DRUG W/O M-CRESOL

| Rat # | Day 1 | Day 3 | Day 7 |
|---|---|---|---|
| E1 | 30.9 | 20.9 | 24.6 |
| E2 | 33.6 | 26.3 | 40.3 |
| E3 | 21.8 | 31.4 | 26.2 |

TABLE 2-continued

DRUG W/O M-CRESOL

| Rat # | Day 1 | Day 3 | Day 7 |
|---|---|---|---|
| E4 | 28.4 | 31.6 | 31.2 |
| E5 | 34.4 | 23.1 | 23.3 |
| E6 | 31.9 | 36.1 | 33.9 |
| E7 | 35.0 | 43.4 | 30.3 |
| E8 | 23.7 | 25.5 | 24.0 |
| E9 | 23.8 | 27.8 | 28.7 |
| E10 | 33.8 | 43.6 | 34.7 |

TABLE 3

DRUG W/M-CRESOL

| Rat # | Day 1 | Day 3 | Day 7 |
|---|---|---|---|
| D1 | 36.2 | 34.8 | 15.2 |
| D2 | 40.7 | 26.4 | 32.1 |
| D3 | 40.2 | 23.7 | 30.7 |
| D4 | 37.0 | 48.5 | 36.5 |
| D5 | 27.5 | 22.5 | 27.3 |
| D6 | 32.5 | 28.7 | 39.7 |
| D7 | 35.1 | 47.5 | 47.9 |
| D8 | 29.4 | 31.2 | 24.8 |
| D9 | 47.9 | 29.9 | 29.9 |
| D10 | 41.0 | 34.1 | 34.6 |

In order to arrive at the change in pain threshold for each animal relative to its baseline, Day 1 responses for each animal was subtracted from each animal's respective responses on Days 3 and 7 and a further correction for placebo effect was applied to the data by subtracting the average value from the saline arm for each day from the data from the other arms for those same days. The results are provided in Tables 4 and 5, below.

TABLE 4

DRUG W/O M-CRESOL

| Rat # | Day 1 | Day 3 | Day 7 |
|---|---|---|---|
| E1 | — | −11.6 | −7.6 |
| E2 | — | −8.9 | 5.4 |
| E3 | — | 8.0 | 3.1 |
| E4 | — | 1.6 | 1.5 |
| E5 | — | −12.9 | −12.4 |
| E6 | — | 2.6 | 0.7 |
| E7 | — | 6.8 | −6.0 |
| E8 | — | 0.2 | −1.0 |
| E9 | — | 2.4 | 3.6 |
| E10 | — | 8.2 | −0.4 |
| AVERAGE | — | −0.3 | −1.3 |

TABLE 5

DRUG W/M-CRESOL

| Rat # | Day 1 | Day 3 | Day 7 |
|---|---|---|---|
| D1 | — | −3.0 | −22.3 |
| D2 | — | −15.9 | −9.9 |
| D3 | — | −18.1 | −10.8 |
| D4 | — | 9.9 | −1.8 |
| D5 | — | −6.6 | −1.5 |
| D6 | — | −5.4 | 5.9 |
| D7 | — | 10.8 | 11.5 |
| D8 | — | 0.2 | −5.9 |
| D9 | — | −19.6 | −19.3 |

TABLE 5-continued

DRUG W/M-CRESOL

| Rat # | Day 1 | Day 3 | Day 7 |
|---|---|---|---|
| D10 | — | −8.5 | −7.7 |
| AVERAGE | — | −5.6 | −6.2 |

A reduction in the force reading (as expressed by the negative number) indicates increasing sensitivity in the animal and therefore increased pain intensity at the infusion site is also increasing.

Referring to the results obtained in Tables 4 and 5, it emerged from these studies that the average pain level in the group treated with treprostinil without m-cresol was substantially less pronounced over the course of the 7 day treatment regimen as compared to the group administered treprostinil containing m-cresol in the formulation, for the same treatment duration. The net changes in response without m-cresol are closer to zero (−0.3 on Day 3 and −1.3 on Day 7) while the net changes in response with m-cresol are of a substantially greater magnitude (−5.6 on Day 3 and −6.2 on Day 7).

Figure 2:
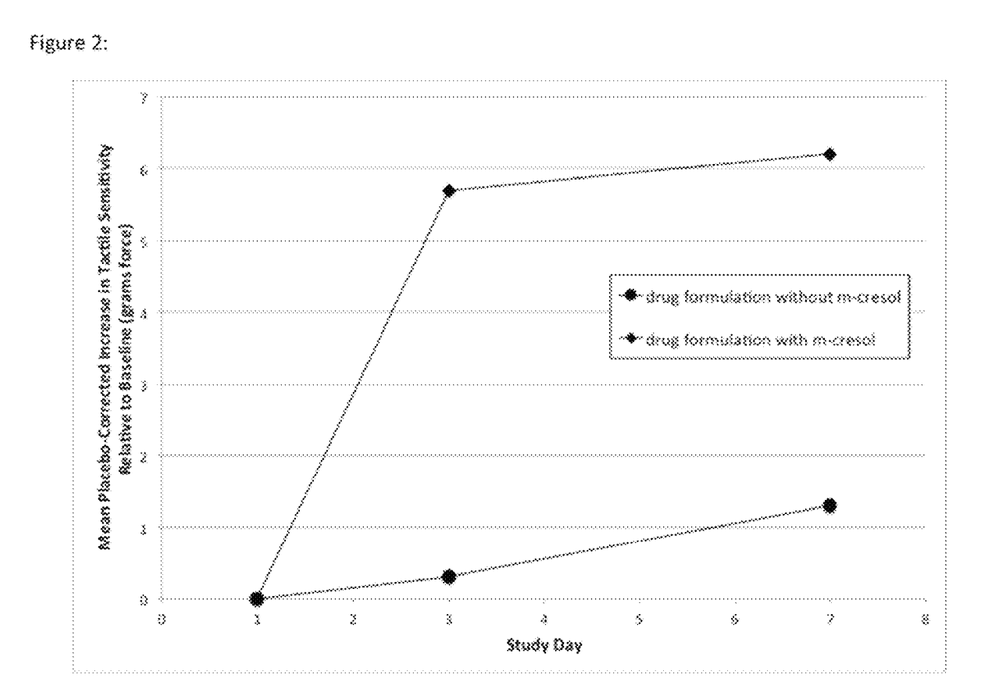
FIG. 2 shows a graphical representation of results with and without m-cresol according to embodiments of the present invention.

FIG. 2 provides a graphical representation of these results.

Taken together, these results demonstrate in an in vivo setting that a unit dosage form of treprostinil in a sterile fluid composition formulated for subcutaneous or intravenous injection, wherein said composition does not comprise an antimicrobial preservative, and provides for unexpectedly significant reduced pain at the site of subcutaneous or intravenous infusion of the treprostinil. In some aspects, this invention contemplates a composition as herein described, containing treprostinil at a dosage of between 0.05 mg/mL and 25 mg/mL. In some embodiments, the treprostinil is provided at a dosage of between 0.1 mg/mL and 50 mg/mL. In some embodiments, the treprostinil is provided at a dosage of between 0.5 mg/mL and 25 mg/mL. As described hereinabove, the treprostinil at a 0.05 mg/mL provided in a sterile fluid composition formulated for subcutaneous or intravenous injection, without antimicrobial preservative, provided for unexpectedly significant reduced pain at the site of subcutaneous or intravenous infusion in rats. As will be appreciated by the skilled artisan, the 0.05 mg/mL concentration chosen yielded a 30 ng/kg/min delivery, which correlates with human doses used, therefore providing comparable dosages ranges, based on human body weights.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above is expressly incorporated herein by reference in their entirety to the same extent as if each were incorporated by reference individually.

What is claimed is:

1. A system comprising a sealed prefilled drug-reservoir containing a unit dosage form of treprostinil in a sterile fluid composition, wherein:
   said composition does not comprise an antimicrobial preservative,
   said treprostinil is present at a dosage of between 0.1 mg/mL and 25 mg/mL,
   said treprostinil is treprostinil sodium,
   said composition comprises sodium chloride, the composition comprises a sodium ion from sodium chloride in a concentration from 3000 to 4500 ppm, and said composition does not comprise metacresol.

2. The system of claim 1, wherein the system is a selectively activatable patch-pump assembly.

3. The system of claim 2, wherein the selectively activatable patch-pump assembly does not comprise a user programmable pump.

4. The system of claim 1, wherein the system is an automatic injection device.

5. The system of claim 1, wherein the volume of the sterile fluid composition does not exceed 10 mL.

6. The system of claim 1, wherein the volume of the sterile fluid composition does not exceed 8 mL.

7. The system of claim 1, wherein the volume of the sterile fluid composition does not exceed 5 mL.

8. The system of claim 1, wherein the volume of the sterile fluid composition does not exceed 2.5 mL.

9. The system of claim 1, wherein the volume of the sterile fluid composition does not exceed 1 mL.

10. The system of claim 1, wherein the system is configured to deliver treprostinil at a rate of 0.5 to 25 mg per day.

11. The system of claim 1, wherein the system is configured to deliver treprostinil at a rate of 0.1 to 25 mg per day.

12. The system of claim 1, wherein the system is formulated for subcutaneous or intravenous injection.

13. The system of claim 1, wherein the sealed prefilled drug-reservoir comprises cyclic olefin polymer.

14. The system of claim 1, wherein the pH of the composition is from 6.5 to 6.7.

15. The system of claim 1, wherein the composition further comprises dextrose or glycerol.

16. The system of claim 1, wherein the composition does not comprise cresols, phenols, parabens, or benzyl alcohol.

* * * * *